(12) United States Patent
Wright et al.

(10) Patent No.: US 8,056,762 B2
(45) Date of Patent: Nov. 15, 2011

(54) DISPENSER

(75) Inventors: Andrew David Wright, Norfolk (GB); Richard Iain Harrison, Buckinghamshire (GB); Colin John Dickens, Northants (GB)

(73) Assignee: Consort Medical PLC, Buckinghamshire (GB)

( * ) Notice: Subject to any disclaimer, the term of this patent is extended or adjusted under 35 U.S.C. 154(b) by 799 days.

(21) Appl. No.: 11/885,624

(22) PCT Filed: Mar. 1, 2006

(86) PCT No.: PCT/GB2006/000722
§ 371 (c)(1),
(2), (4) Date: Jul. 7, 2008

(87) PCT Pub. No.: WO2006/092590
PCT Pub. Date: Sep. 8, 2006

(65) Prior Publication Data
US 2009/0166379 A1    Jul. 2, 2009

(30) Foreign Application Priority Data
Mar. 3, 2005   (GB) .................................. 0504441.7

(51) Int. Cl.
*B67D 1/00*   (2006.01)

(52) U.S. Cl. ........ 222/82; 222/209; 222/633; 222/321.2
(58) Field of Classification Search .............. 222/80–83, 222/209, 633, 321.2
See application file for complete search history.

(56) References Cited

U.S. PATENT DOCUMENTS

| 4,017,007 | A | | 4/1977 | Riccio | |
| 5,411,175 | A | * | 5/1995 | Armstrong et al. | .......... 222/83.5 |
| 5,944,222 | A | | 8/1999 | Fuchs et al. | |
| 6,398,074 | B1 | * | 6/2002 | Bruna et al. | .................... 222/82 |

(Continued)

FOREIGN PATENT DOCUMENTS

EP    1 329 237    7/2003

(Continued)

*Primary Examiner* — Kevin P Shaver
*Assistant Examiner* — Melvin Cartagena
(74) *Attorney, Agent, or Firm* — Smith, Gambrell & Russell, LLP

(57) ABSTRACT

A hand-held dispenser for dispensing a pharmaceutical product is disclosed. The dispenser has a housing providing a duct. A frangible membrane is provided in the duct. A probe with a piercing tip is mounted in the duct and arranged such that, in use the piercing tip pierces the frangible membrane. An air compression device is provided to compress air for expelling a pharmaceutical product through the probe and a channel is provided to substantially equalise the pressure in the air compression device and the pressure above the frangible membrane. The ability to substantially equalise the pressure in the bellows and the pressure above the frangible membrane on the sheath provides for a mote consistent release of pharmaceutical product when the frangible membrane is pierced. This is because the compressed air from the bellows which expels the pharmaceutical product through the probe does not encounter a sudden change in pressure as it passes the pierced frangible membrane with the entrained pharmaceutical product. In use, when compressed air is used to expel a pharmaceutical product through the probe, the air path through the probe has a lower resistance than the channel to substantially equalise the pressure in the air compression device and the pressure above the frangible membrane. This ensures that the majority of the compressed air is used to expel the pharmaceutical product. The piercing tip preferably comprises a generally annular cutting edge on an end portion of the probe with an interruption in the generally annular cutting edge.

15 Claims, 4 Drawing Sheets

U.S. PATENT DOCUMENTS

| | | |
|---|---|---|
| 6,866,039 B1 | 3/2005 | Wright et al. |
| 6,945,953 B2 | 9/2005 | Wright |
| 7,270,127 B2 * | 9/2007 | Lockhart et al. ......... 128/203.15 |
| 2003/0127533 A1 * | 7/2003 | Stihl ................................. 239/8 |
| 2004/0050885 A1 * | 3/2004 | Stradella ....................... 222/633 |

FOREIGN PATENT DOCUMENTS

| | | |
|---|---|---|
| GB | 2367756 | 4/2002 |
| GB | 2 422 786 | 5/2007 |
| WO | 03/061745 | 7/2003 |

* cited by examiner

DISPENSER

The present invention relates to a dispenser, in particular a dispenser with a frangible membrane which is pierced during use to release a product, such as a medicament.

A dispenser with a frangible membrane is disclosed for example in GB 2,367,756. The frangible membrane keeps the product to be dispensed sealed prior to use to prevent leakage of any of the product and provides protection against contamination or ingress of moisture from the air for example. It is particularly desirable to protect powdered product from moisture because when in contact with moisture, the powder becomes less free flowing and harder to dispense. In GB 2,367,756 a probe with a piercing tip is provided slidably within a duct. A product to be dispensed, such as a powdered medicament, is provided in the probe and a sheath with a frangible membrane is provided over the piercing tip of the probe to seal the product in the probe. Upon actuation, the probe and sheath are slid along the duct until the sheath engages an annular shoulder preventing its further movement and the piercing tip of the probe pierces the frangible membrane on the sheath and the product is dispensed using compressed air from a bellows.

The dispenser disclosed in GB 2,367,756 provides good protection for the product to be dispensed using the frangible membrane.

It is an aim of an embodiment of the present invention to be able to discharge even larger proportions of the product to be dispensed than GB 2,367,756.

According to a first aspect of the present invention there is provided a hand-held dispenser for dispensing a pharmaceutical product, the dispenser comprising a housing providing a duct;

a frangible membrane provided in the duct;

a probe with a piercing tip mounted in the duct, the probe being arranged such that, in use, the piercing tip pierces the frangible membrane;

an air compression device to compress air for expelling a pharmaceutical product through the probe; and a channel to substantially equalise the pressure in the air compression device and the pressure above the frangible membrane.

The ability to substantially equalise the pressure in the air compression device and the pressure above the frangible membrane provides for a more consistent release of pharmaceutical product when the frangible membrane is pierced. This is because the compressed air from the air compression device which expels the pharmaceutical product through the probe, the piercing tip and the pierced frangible membrane does not encounter a sudden change in pressure as it passes with the entrained pharmaceutical product into the duct through the pierced frangible membrane. A sudden increase or decrease in pressure as the compressed air with entrained pharmaceutical product passes through the pierced frangible membrane would impede the flow of compressed air and pharmaceutical product reducing the amount discharged and providing a less consistent discharge.

The channel substantially equalises the pressure in the air compression device and the pressure above the frangible membrane on the side of the frangible membrane opposite to that on which the probe is initially provided.

The probe may be arranged to be slid in the duct.

The channel is preferably provided as a gap between the inside surface of the duct and the outside surface of the probe or a sheath mounted on the probe.

In use, when compressed air is used to expel a pharmaceutical product through the probe, the air path through the probe has a lower resistance than the channel which substantially equalises the pressure in the air compression device and the air pressure above the frangible membrane. This ensures that the majority of the compressed air is used to expel the pharmaceutical product.

The frangible membrane is preferably provide at one end portion of a sheath which has a first larger diameter portion and a second smaller diameter portion defining an external shoulder therebetween to engage with a corresponding internal shoulder on the inside surface of the duct and a spacer is preferably provided on one or both of the shoulders to maintain the channel past the engaged shoulders. The spacer may for example be one or more of a recess, a protrusion or a rib or a combination of these.

One or more spacers, which may for example be one or more of a recess protrusion or rib, may be provided on the inside surface of the duct or the outside surface of the sheath to maintain the gap forming the channel therebetween.

The air compression device may be a bellows, a plunger or a pump for example.

Alternatively or additionally the frangible membrane may be mounted to the duct.

According to a second aspect of the present invention the piercing tip preferably comprises a generally annular cutting edge with an interruption therein. The piercing tip is preferably the end portion of a cylindrical probe for housing the product to be dispensed. The interruption in the generally annular cutting edge of the piercing tip enables a portion of the frangible membrane to remain attached to the duct or sheath on which it is provided, so that the frangible membrane does not become completely detached from the duct or sheath and interfere with the dispensing of the product. Furthermore the interruption in the generally annular cutting edge enables the frangible membrane to be pierced at the same point every time providing a consistent dispensed product spray pattern so that dispensed product can be directed for example to a particular portion of a nasal cavity.

The duct may be sealed at a portion nearer to an outlet than where the probe and sheath are provided. The seal may be for example, a further frangible membrane which could also be pierced by the piercing tip or a removable cap.

Embodiments of the present invention will now be described, by way of example only, with reference to the accompanying drawings, in which.

Figure 1:
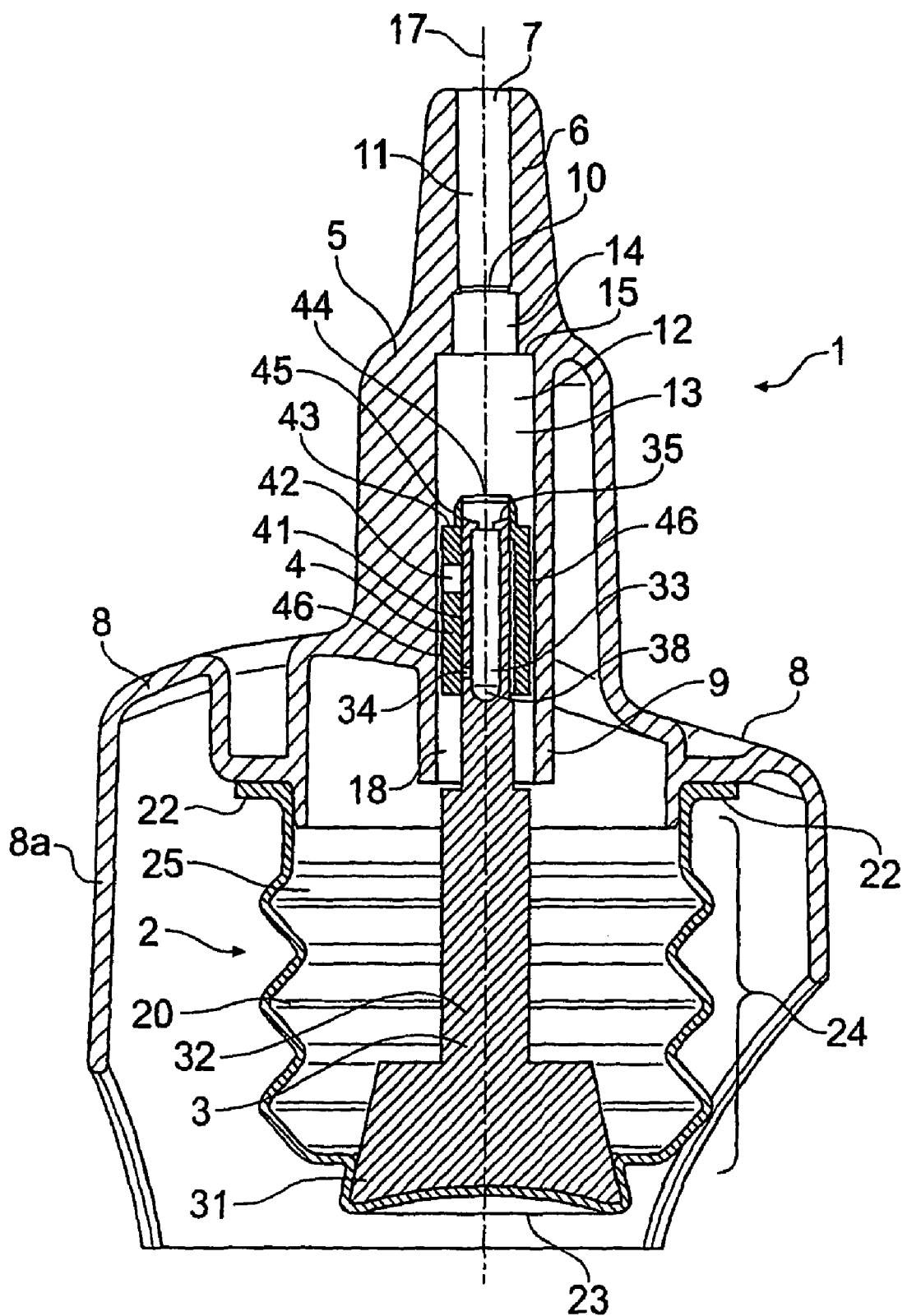
FIG. 1 is a cross-sectional view of the dispenser according to the present invention in a storage condition.
Figure 2:
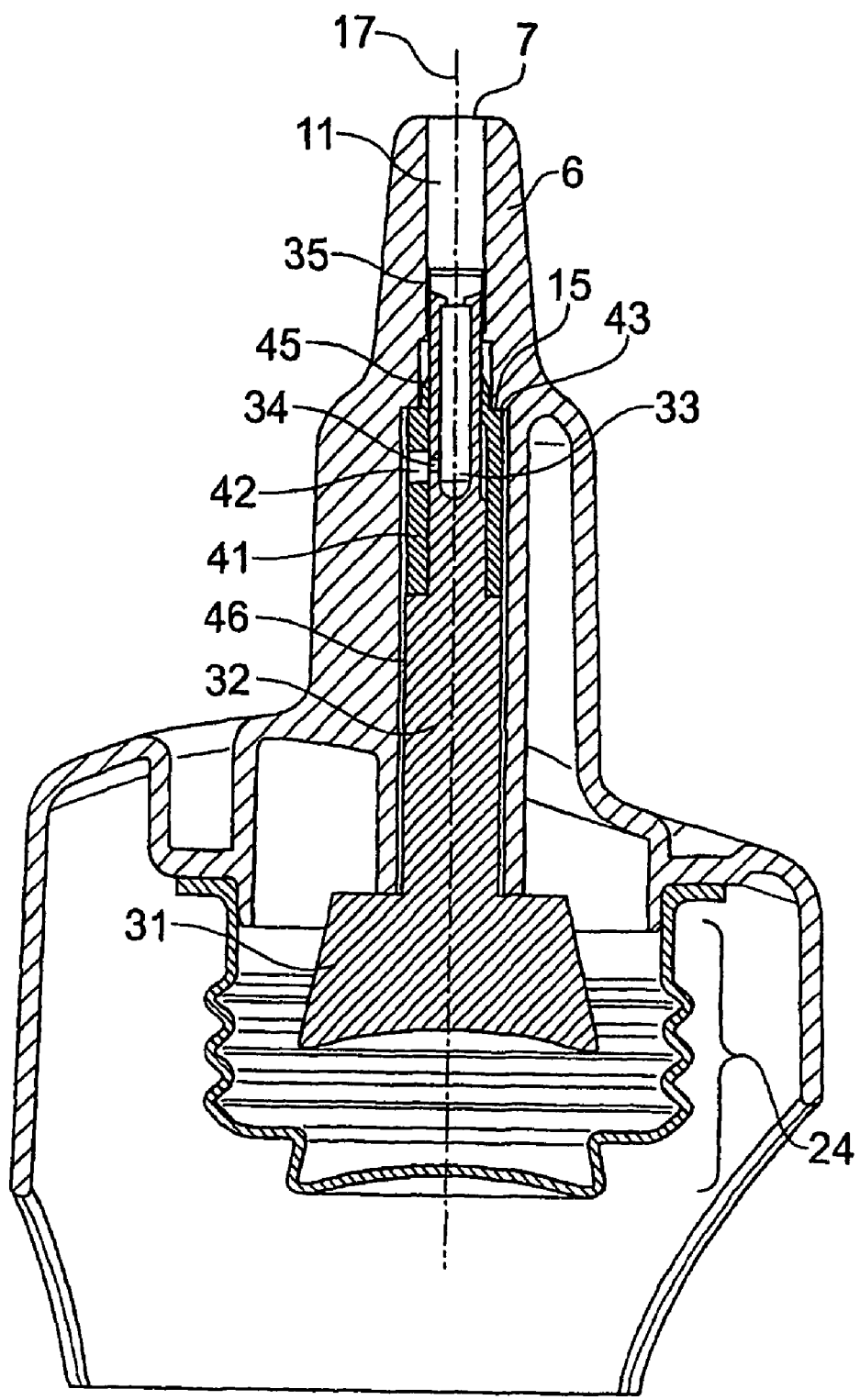
FIG. 2 is a cross-sectional view of the dispenser of FIG. 1 in a dispensing position.

As shown in FIGS. 1 and 2, a first embodiment of the present invention comprises a housing 1 having a generally cylindrical section 5, a tip 6 and finger rests 8. The cylindrical section 5 of the housing 1 is provided with an internal, axially orientated, tubular extension 9. A bore of the tubular extension 9 is closed off partway along its length by a first frangible membrane 10. The bore defines a duct 12 extending from the first frangible membrane 10 in a direction of an open end 18 of the tubular extension 9 and an outlet duct 11 extending from the first frangible membrane 10 in a direction of the tip 6. The extremity of the outlet duct 11 distal the first frangible membrane 10 defines an outlet 7 in tip 6. The duct 12 and outlet duct 11 preferably both extend along a longitudinal axis 17 of the housing 1.

The duct 12 has a first bore 13 of larger diameter and a second bore 14 of narrower diameter with an annular internal shoulder 15 provided therebetween.

The finger rests 8 may be formed by a single annular flange extending from the cylindrical section 5 or by two or more separate flanges circumferentially spaced around the cylindrical sections 5. The finger rests 8 have a skirt 8a extending therefrom.

A bellows unit 2 is joined to the housing 1. The bellows unit 2 comprises an annular mounting flange 22 and an axially extending bellows portion 24 having a plurality of concertina formations 20 formed therein. An end of the bellows unit 2 distal the mounting flange 22 is closed off by an end face 23 defining a finger or thumb rest.

A probe 3 is provided within the bellows unit 2 and housing 1. The probe 3 comprises a cylindrical extension 32 which is mounted by means of a flange 31 to the inside of end face 23 of the bellows unit 2 so as to lie extending substantially along longitudinal axis 17. The cylindrical extension 32 comprises a hollow portion at an end distal the flange 31 defining a powder storage chamber 33. The storage chamber 33 is provided with a hemi-spherically shaped lower end 38 which is believed to lead to a more efficient entrainment and removal of the powdered product from the storage chamber 33. Alternatively the lower end may be V-shaped or U-shaped in cross-section. The distal end of the cylindrical extension 32 is shaped to form a piercing tip 35 described in more detail later. A radially directed aperture 34 is provided in the wall of the cylindrical extension 32 communicating with the storage chamber 33.

A sheath 4 is slidably mounted on the cylindrical extension 32. The sheath 4 comprises a cylindrical portion 41 having a radially orientated aperture 42 therein and a smaller diameter portion 45. The sheath 4 is closed at one end by a second frangible membrane 44. The junction between the cylindrical portion 41 and the smaller diameter portion 45 defines an external annular shoulder 43. The internal diameter of the sheath 4 is such that sliding movement between the sheath 4 and probe 3 is facilitated while maintaining an air-tight seal therebetween. Optionally sliding seal members (not shown), such as O-rings, may be provided between the sheath 4 and probe 3 to improve the seal integrity.

The product to be dispensed, in this example a powdered product, is held in the storage chamber 33.

Before use, in a storage condition as shown in FIG. 1, the sheath 4 is mounted on probe 3 with the piercing tip 35 in close proximity to or abutting against the second frangible membrane 44. In this position the radial apertures 34 and 42 are out of alignment and there is consequently no open path between an interior 25 of the bellows portion 24 and the storage chamber 33. Thus, the apertures 34 and 42, which together form an inlet valve, are in a 'closed' position.

A channel 46 is provided from the volume in the duct 12 above the second frangible membrane 44 on the top of the sheath 4 (on the opposite side of the frangible membrane 44 from the probe 3) to an interior 25 of the bellows 2. In this example the channel 46 is provided by the outside diameters of the cylindrical portion 41 of the sheath 4 and the smaller diameter portion 45 of the sheath 4 and the inside diameters of the first 13 and second 14 bores of the duct 12 being selected to provide gaps therebetween. These gaps enable air to be expelled from above the second frangible membrane 44 as the probe 3 and sheath 4 slide through the duct 12 towards the first frangible membrane 10.

Figure 5:
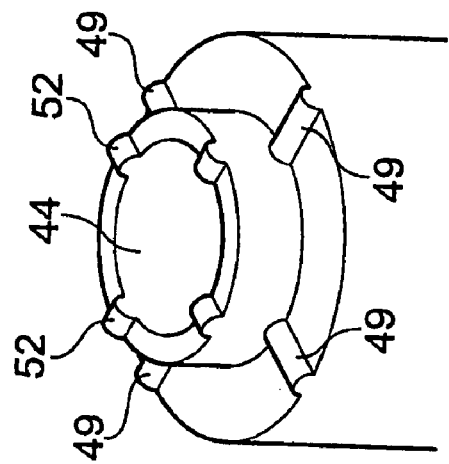
FIG. 5 is a perspective view of a third example of spacers on an external annular shoulder of a sheath surrounding a probe and FIG. 6 is a perspective view of a piercing tip.
Figure 4:
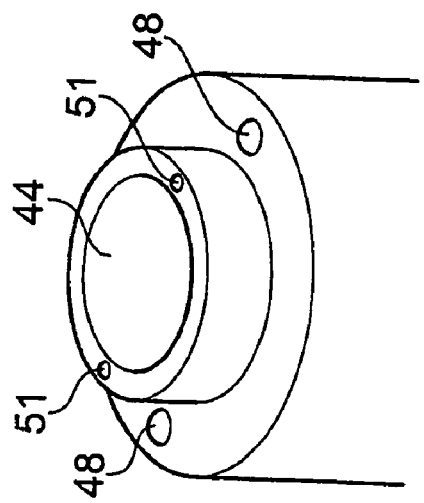
FIG. 4 is a perspective view of a second example of spacers on an external annular shoulder of a sheath surrounding a probe.
Figure 3:
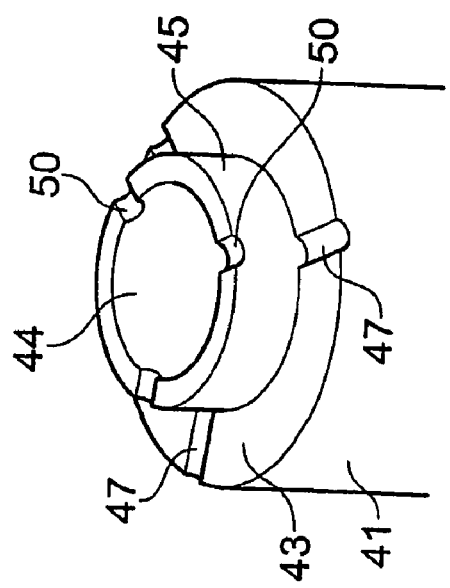
FIG. 3 is a perspective view of a first example of spacers on an external annular shoulder of a sheath surrounding a probe.

One or more axial spacers are provided on or between the external annular shoulder 43 and the internal shoulder 15 to provide an air passage between the second 14 and the first 13 bores of the duct 12 when the probe 3 and sheath 4 are inserted into the second narrower bore 14 as shown in FIG. 2. These one or more spacers may for example, take the form of one or more recesses 47 in the external annular shoulder 43 as shown in FIG. 3, one or more protrusions 48 on the external annular shoulder 43 as shown in FIG. 4, one or more ribs 49 on the external annular shoulder 43 as shown in FIG. 5 or any number and combination of recesses, protrusions and ribs. Alternatively or additionally one or more spacers such as any number of combination of recesses, protrusions and ribs may be provided on the underside of the annular internal shoulder 15 (not shown).

Spacers 50, 51, 52 may also be provided at the top of the reduced diameter portion 45 or the underside of the top of the second narrower diameter portion 14 of the duct 12 (not shown) to enhance the channel 46 from above the second frangible member 44. These spacers may, for example, take the form of one or more recesses 50 as shown in FIG. 3, one or more protrusions 51 as shown in FIG. 4, one or more ribs 52 as shown in FIG. 5 or any number or combination thereof. Alternatively or additionally one or more spacers, which may for example comprise any number or combination of recesses, protrusions or ribs (not shown) may be provided on the underside of the top of the second narrower diameter portion 14 of the duct 12.

If desired, circumferential spacers may be provided on one or both of the outside surface of the cylindrical portion 41 and the inside surface of the first bore 13 of the duct 12 and/or on one or both of the outside circumference of the smaller diameter portion 45 and the inside surface of the second bore 14 of the duct 12 to ensure the maintenance of the channel forming gap 46 therebetween. These circumferential spacers may, for example take the form of one or more recesses, protrusions or ribs.

Figure 6:
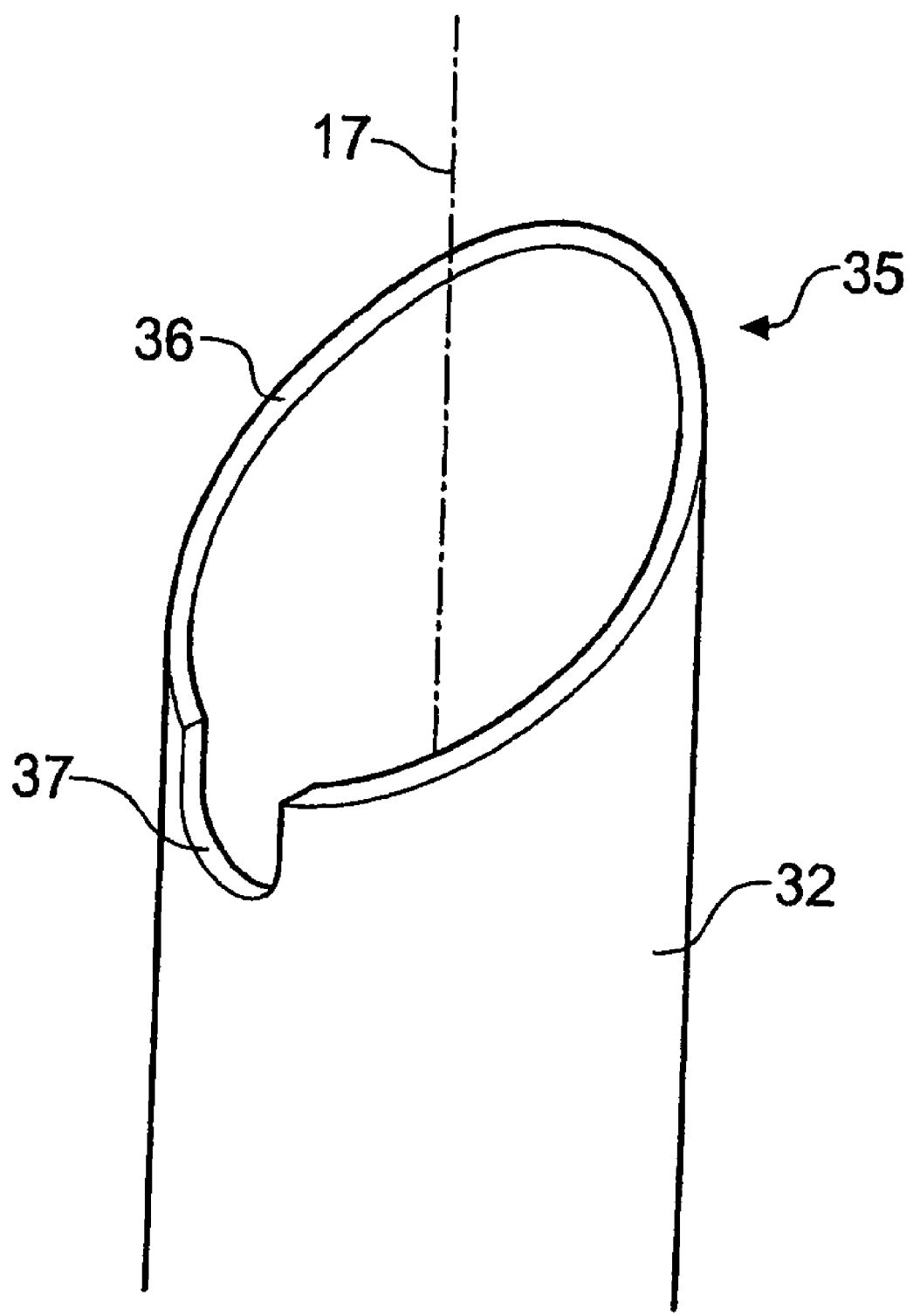

FIG. 6 shows an enlarged view of the piercing tip 35 at the distal end of the cylindrical extension 32. As can be seen the piercing tip 35 comprises the end of the cylindrical extension 32 which is inclined to the perpendicular or non-orthogonal to the axis 17. The cutting edge 36 at the end of the cylindrical portion 32 is substantially annular with an interruption or cut-out 37 therein. In use, when the generally annular cutting edge 36 of the piercing tip 35 penetrates the frangible membranes 10, 44, the non-cutting interruption 37 does not pierce the frangible membranes 10, 44 leaving a portion of the frangible membranes 10, 44 connected to the duct 12 and sheath 4 respectively whilst the dispenser dispenses its contents. The non-cutting interruption does not cut the frangible membranes because it is arranged to have sufficient depth such that it does not reach the frangible membranes when the external annular shoulder 43 of the sheath 4 engages the internal annular shoulder 15 of the duct 12. Furthermore, the base of the interruption or cut-out portion is preferably blunt to prevent it from cutting a membrane. As the frangible membranes 10, 44 remain attached to the duct 12 and sheath 4 at predetermined points they do not interfere with the dispensing of the product so a more reliable and reproducible flow pattern is obtained. Furthermore, as the frangible membranes are not detached, they are not dispensed with the pharmaceutical product into a user's nose or mouth for example.

The housing 1, probe 3 and sheath 4 are manufactured from polyethylene or polypropylene or similar material. Similarly, the frangible membranes 10, 44 are manufactured from polyethylene or polypropylene or similar material. Alternatively, the probe 3 may be manufactured from a metal such as stainless steel.

The bellows unit 2 is manufactured from polyethylene, polypropylene, a thermoplastic elastomer or other similarly flexible polymer. The unit 2 may be formed from a single moulding of a single material. Alternatively, the unit 2 may be formed as a two-part moulding, each part being of a different material.

Advantageously, the materials of the dispenser lend themselves to easy and ready recycling. In the preferred arrangement, the absence of any metallic or ceramic components reduces the cost of processing the recycled material.

Advantageously, the components of the dispenser are moulded. This leads to low levels of material waste. The current design allows for a low number of individual parts which reduces assembly time and cost. For example, the whole apparatus may be formed from only three components, the first component being the housing 1 including the first frangible membrane 10, the second component being the bellows unit 2 and probe 3 formed as a unitary part, and the third component being the sheath 4 including the second frangible membrane 44.

In use, a user holds the apparatus typically by means of two or more fingers positioned on the finger rests 8 and a thumb positioned on end face 23. The top 6 is then inserted into the nose (or mouth if the apparatus is for pulmonary use or any other orifice for any other use). Inhalation at this stage is ineffective since the first frangible membrane 10 seals off the outlet duct 11.

The user depresses the end face 23 of the bellows unit 2 so as to move the probe 3 and sheath 4 axially into housing 1 in the direction of tip 6. Initially, the probe 3 and sheath 4 are free to move unhindered with the smaller diameter portion 45 of the sheath 4 being slidingly received in the second narrower portion 14 of the duct 12.

As the probe 3 and sheath 4 slide though the duct 12 towards the first frangible membrane 10, air above the second frangible membrane 44 escapes from the reducing volume above the second frangible membrane 44 via channel 46. Further movement of the probe 3 and sheath 4 brings the external shoulder 43 of the sheath 4 into contact with the internal shoulder 15 of the duct 12 via spacers 47, 48 or 49 with air escaping from the second narrower portion 14 of the duct 12 through the spacers 47, 48, 49, 50, 51, 52. At this point, further inward movement of the sheath 4 relative to the duct 12 is prevented. Continued inward movement of the probe 3 causes the piercing tip 35 of the probe 3 to pierce and break the second frangible membrane 44. Subsequent inward movement of the probe 3 then causes the piercing tip 35 to pierce and break the first frangible membrane 10 opening communication between the duct 12 and outlet duct 11. Advantageously, both of the frangible membranes 44, 10 are ruptured from below with the piercing means 35 moving relative to the membranes in the direction of the tip 6. As a result the 'flap' of the membrane which is left connected to the sheath 4 and duct 12 respectively because of the interruption 37 in the generally annular cutting edge of the piercing tip 35 after rupture is positioned above the membrane periphery such that as gas passes the membrane the 'flap' tends to be moved away from the hole formed in the membrane so as not to block the flow path unlike where a membrane is ruptured from above. Furthermore, as the membranes remain attached to the sheath 4 and duct 12 at predetermined points, they do not interfere with the dispensed product and a more reproducible flow pattern is obtained. A gap is preferably provided above the frangible membranes 10, 44 in the actuated device to accommodate the flaps provided by the pierced frangible membranes 10, 44.

As the piercing tip 35 passes through the first frangible membrane 10 barbs (not shown) or other snap-fit formations may be engaged and retained with an annular lip of the first frangible membrane 10, preventing retraction of the probe 3 in the direction of the bellows unit 2. Advantageously, the barbs prevent any attempt at reuse of the dispensing apparatus and also provide a clear visual indication that the apparatus has been used.

The axial length of the smaller diameter portion 45 of the sheath 4 and the duct 12 can be chosen such that the first and second frangible membranes lie in close proximity at the point of rupture ensuring that the user feels a single, positive sensory signal that the storage chamber 33 has been opened.

Simultaneously with the first and second membranes being ruptured, the relative axial movement of the sheath 4 and probe 3 causes the apertures 34 and 42 to come into alignment, opening the inlet valve of the storage chamber 33. The apparatus is now in the 'dispensing' position, as shown in FIG. 2. In the dispensing position the inlet valve is open and the first and second frangible membranes are ruptured. Thus a continuous flow path is established between the interior 25 of the bellows portion 24 and the outlet 7. As a result air, pressurised during inward movement of the bellows unit's concertinas 20, is displaced from the interior 25 of the bellows portion 24, through the inlet valve formed by the apertures 34 and 42 and into the storage chamber 33 where it entrains the powdered product. The air and entrained product is then displaced through the piercing tip 35 and does not encounter any impedance from an increase or reduction in pressure above the pierced second frangible membrane 44 because of the pressure equalisation produced by the channel 46 and continues unhindered through duct 12 and outlet duct 11 where it finally exits outlet 7. In this way the apparatus actively dispenses the powder so that the necessary inhalatory effort required by the user is reduced or even effectively eliminated.

In use, when compressed air is used to expel a pharmaceutical product through the probe, the air path through the probe has a lower air resistance than the equalising channel 46 to ensure that the majority of compressed air is used to expel the pharmaceutical product.

The degree of compression and pressurisation of the air within bellows unit 2 provides adequate energy to efficiently entrain and dispense the powdered product with little or no inhalatory effort by the user. Advantageously, this means that the apparatus may be used for dispensing products to users who can provide little inhalatory effort such as children or the elderly as well as to users who are unable to provide any inhalatory effort such as those who are unconscious. Furthermore, since no inhalatory effort is required by the user, a reproducible spray pattern may be achieved to promote delivery of a medicament to a desired area, for example a predetermined portion of a nasal cavity.

Many modifications may be made to the example described above whilst still falling within the scope of the invention. For example the channel 46 could be any suitable flow path such as for example a conduit provided in the cylindrical section 5 connecting the top of the second frangible membrane 44 to the interior of the bellows 2 directly. The first frangible membrane 10 could be replaced by a removable cap (not shown) or omitted. If used, the first frangible membrane 10 could be pierced by any suitable means such as by a piercing tip (not shown) passed down through outlet 11. Instead of the bellows unit 2 described above, any suitable air compression device could be used such as, for example a plunger or a pump.

The invention claimed is:

1. A hand-held dispenser for dispensing a pharmaceutical product, the dispenser comprising:
    a housing providing a duct;
    a frangible membrane provided in the duct;
    a probe with a piercing tip mounted in the duct, the probe being arranged such that, in use, the piercing tip pierces the frangible membrane;
    an air compression device to compress air for expelling a pharmaceutical product through the probe; and
    a channel to substantially equalise the pressure in the air compression device and the pressure above the frangible membrane,.
    wherein the frangible membrane is provided on a sheath which comprises a first larger diameter portion and a second axially spaced smaller diameter portion defining an external shoulder therebetween, and the inside surface of the duct has a corresponding internal shoulder to be engaged by the external shoulder of the sheath and an axial spacer is provided on one or both of the external and internal shoulders to maintain the channel past the engaged shoulders.

2. A dispenser according to claim 1, wherein an air path through the probe for expelling a pharmaceutical product has a lower resistance than the channel.

3. A dispenser according to claim 1, wherein the channel comprises a gap between the inside surface of the duct and the outside surface of the probe or a sheath mounted on the probe.

4. A dispenser according to claim 3, wherein a circumferential spacer is provided on one or both of the inside surface of the duct and the outside surface of the probe or sheath.

5. A dispenser according to claim 4, wherein the circumferential spacer comprises one or more of a recess, a projection and/or a rib.

6. A dispenser according to claim 3, wherein an axial spacer is provided on the distal end of the probe or sheath.

7. A dispenser according to claim 1, wherein the axial spacer comprises one or more recesses.

8. A dispenser according to claim 1, wherein the axial spacer comprises one or more protrusions.

9. A dispenser according to claim 1, wherein the axial spacer comprises one or more ribs.

10. A dispenser according to claim 1, wherein the piercing tip comprises a generally annular cutting edge on an end portion of the probe with an interruption in the generally annular cutting edge.

11. A dispenser according to claim 10, wherein the generally annular cutting edge is in a plane which is non-orthogonal to an axis of the probe.

12. A dispenser according to claim 11, wherein the non-orthogonal plane has an upper end and a lower end and the interruption is at the lower end.

13. A hand-held dispenser for dispensing a pharmaceutical product, the dispenser comprising
    a housing providing a duct;
    a probe with a piercing tip slidably mountable within the duct to pierce a frangible membrane, in use, to enable a product to be dispensed through the duct
    wherein the piercing tip comprises a generally annular cutting edge on an end portion of the probe with an interruption in the generally annular cutting edge,.
    wherein the frangible membrane is provided on a sheath which comprises a first larger diameter portion and a second axially spaced smaller diameter portion defining an external shoulder therebetween, and the inside surface of the duct has a corresponding internal shoulder to be engaged by the external shoulder of the sheath and an axial spacer is provided to maintain a channel past the engaged shoulders.

14. A dispenser according to claim 13, wherein the generally annular cutting edge is in a plane which is non-orthogonal to an axis of the probe.

15. A hand-held dispenser according to claim 13, wherein the non-orthogonal plane has an upper end and a lower end and the interruption is provided at the lower end.

* * * * *